United States Patent
Sugamata

(10) Patent No.: US 7,119,076 B2
(45) Date of Patent: Oct. 10, 2006

(54) PREVENTIVES OR REMEDIES FOR ENDOMETRIOSIS OR UTERINE MYOMA

(76) Inventor: Masao Sugamata, 2308-3, Minamiakatsuka, Nogi-machi, Shimotsuga-gun, Tochigi 329-0112 (JP)

( * ) Notice: Subject to any disclaimer, the term of this patent is extended or adjusted under 35 U.S.C. 154(b) by 0 days.

(21) Appl. No.: 10/416,802

(22) PCT Filed: Nov. 15, 2001

(86) PCT No.: PCT/JP01/09972

§ 371 (c)(1),
(2), (4) Date: Jul. 10, 2003

(87) PCT Pub. No.: WO02/40036

PCT Pub. Date: May 23, 2002

(65) Prior Publication Data

US 2004/0198675 A1    Oct. 7, 2004

(30) Foreign Application Priority Data

Nov. 15, 2000   (JP)   ............... 2000-347643

(51) Int. Cl.
*A61K 31/70*    (2006.01)

(52) U.S. Cl. .......................................... 514/29; 514/30
(58) Field of Classification Search .................. 514/29, 514/30

See application file for complete search history.

(56) References Cited

U.S. PATENT DOCUMENTS 5,605,889 A * 2/1997 Curatolo et al. ............... 514/29
5,958,888 A * 9/1999 Macy et al. .................. 514/29

OTHER PUBLICATIONS

Mikamo et al., Chermotherapy, vol. 44, pp. 50-54 (1998).
Mikamo et al., Chermotherapy, vol. 43, pp. 148-152 (1997).
Granovsky-Grisaru et al., Am. J. Obset. Gynecol., vol. 178, No. 1, Part 1, pp. 171-174 (1998).

* cited by examiner

*Primary Examiner*—Elli Peselev
(74) *Attorney, Agent, or Firm*—Birch, Stewart, Kolasch & Birch, LLP

(57) ABSTRACT

A drug effective for prevention and therapy of endometriosis and hysteromyoma is disclosed. The drug for prevention and/or therapy of endometriosis and/or hysteromyoma according to the present invention comprises as an effective ingredient a macrolide antibiotic.

3 Claims, No Drawings

PREVENTIVES OR REMEDIES FOR ENDOMETRIOSIS OR UTERINE MYOMA

This application is the national phase under 35 U.S.C. § 371 of PCT International Application No. PCT/JP01/09972 which has an International filing date of Nov. 15, 2001, which designated the United States of America.

TECHNICAL FIELD

The present invention relates to a drug for prevention and/or therapy of endometriosis and/or hysteromyoma.

BACKGROUND ART

Endometriosis is a disease wherein endometrium or endometrium-like tissue ectopically proliferates at a site other than the inner surface of the cavity of uterus which is the natural site thereof. The cause of endometriosis is unknown, and therapies such as separation of the adhered tissues by surgery, administration of hormones and administration of analgesics are performed. However, these therapies are symptomatic treatments, and no complete therapy exists.

Hysteromyoma is benign tumor formed on the muscle of uterus, and may cause emmeniopathy and metrorrhagia. If the myoma is large, it compresses ambient organs, so that congestion in the pelvis, lumbago or dragging pain likely to occur. There is no therapy of hysteromyoma other than surgery, and the surgery is total extirpation of uterus in principle. Pharmacotherapy of hysteromyoma is not performed.

DISCLOSURE OF THE INVENTION

An object of the present invention is to provide a drug effective for prevention and/or therapy of endometriosis and/or hysteromyoma.

The present inventors intensively studied to discover that macrolide antibiotics are effective for prevention and/or therapy of endometriosis and/or hysteromyoma, thereby completing the present invention.

That is, the present invention provides a drug for prevention and/or therapy of endometriosis and/or hysteromyoma, comprising a macrolide antibiotic as an effective ingredient. The present invention also provides a use of a macrolide antibiotic for the production of a drug for prevention and/or therapy of endometriosis and/or hysteromyoma. The present invention further provides a method for prevention and/or therapy of endometriosis and/or hysteromyoma, comprising administering a macrolide antibiotic to a patient suffering from endometriosis and/or hysteromyoma, in an amount effective for the prevention and/or therapy of endometriosis and/or hysteromyoma.

By the present invention, a drug effective for prevention and therapy of endometriosis, which can cure endometriosis was first provided. The number of patients suffering from endometriosis is now rapidly increasing, and endometriosis is now one of the main causes of menorrhalgia and infertility. Thus, the present invention is thought to greatly contribute in the field of therapy of infertility, and therapy and prevention of menorrhalgia. Further, macrolide antibiotics are effective for prevention and therapy of hysteromyoma of which pathological symptoms are similar to those of endometriosis.

BEST MODE FOR CARRYING OUT THE INVENTION

As mentioned above, the drug for prevention or therapy of endometriosis according to the present invention is effective for both prevention and therapy of endometriosis, and comprises a macrolide antibiotic as an effective ingredient.

Macrolide antibiotics means a group of antibiotics having lactone rings (12- to 16-membered lactone ring (the number of atoms constituting the ring is 12 to 16), and having (a) neutral or (an) amino sugar(s). Examples of the macrolide antibiotics which may be employed in the present invention include clarithromycin, roxithromycin, azithromycin, erythromycin, josamycin, leucomycins, spiramycins, carbomycins, tylosin, angolamycin, kitasamycin, acetylspiramycin, midecamycin, oleandomycin, mirosamycin and maridomycin, as well as hydrates, non-toxic salts and derivatives thereof, although not restricted thereto. The term "derivative" herein means those compounds having the same basal skeleton as the original compound, but the substituents attached to the lactone ring and/or sugar(s) are changed, and such derivatives may be used as long as they have antibiotic properties. Examples of the non-toxic salt include hydrochloric acid salt, sulfuric acid salt, tartaric acid salt and citric acid salt, although the non-toxic salts are not restricted thereto. As the macrolide antibiotic, those having 14-membered or 15-membered lactone ring are preferred, and those in which two sugar units are bound are preferred. Especially, clarithromycin, roxithromycin and azithromycin are preferred.

The drug for prevention and/or therapy of endometriosis according to the present invention may be administered by oral administration or parenteral administration such as intravenous, subcutaneous, intramuscular or rectal administration, and oral administration is preferred because it is simple. Although the administration dose is appropriately selected depending on the degree of the symptom of the patient, type of the macrolide antibiotic and the like, the dose is usually about 300 to 500 mg in terms of the amount of the macrolide antibiotic per day per adult. The drug is effective at the dose employed for the therapies of infectious diseases.

Adenomyosis of uterus is the state that the endometrium or endometrium-like tissue ectopically proliferates in myometrium, so that it is a form of endometriosis and is included in endometriosis ("Surgical Pathology", p. 713–715, published by Bunkodo; "Clinical Histopathology", p.661, published by Kyorin Shoin).

The present inventor intensively studied the findings of hysteromyoma. As a result, existence of mast cells and degranulation were observed. Thus, it was confirmed that the findings thereof are the same as the endometriosis from the observation of human cases. Therefore, macrolide antibiotics are effective for the therapy and prevention of hysteromyoma, similarly to endometriosis.

As for the macrolide antibiotics used for the therapy and/or prevention of hysteromyoma, as well as the administration route and administration dose, the above-described explanations for the endometriosis can be applied as they are.

As for the formulation of the drug, any formulation methods ordinarily employed in the field of pharmaceuticals may be employed. For example, the macrolide antibiotic may be granulated together with an additive such as a polyoxyethylenesorbitan fatty acid ester, propylene glycol or sodium laurate, and the resultant may be made into tablets, but the formulation method is not restricted thereto.

For example, a drug may be formulated by mixing 50 mg of clarithromycin and 34 mg of polyoxyethylenesorbitan fatty acid ester, granulating the resulting mixture and making tablets from the granulated mixture. Needless to say, the formulation method is not restricted thereto.

Since macrolide antibiotics have been used as therapeutic agents for various infectious diseases, safeties thereof to the extent demanded for pharmaceuticals have been confirmed.

The present invention will now be described more concretely by way of examples. However, the present invention is not limited to the following examples.

EXAMPLE 1

Therapeutic Effect for Endometriosis by Clarithromycin

Endometriosis model rats were prepared by the method described in Michael W. Vernon et al., FERTILITY AND STERILITY, Vol. 44, No. 5, Nov. 1985. That is, endometriosis model rats were prepared as follows: Sprague-Dawley rats (female) of 8 weeks old were acclimatized for 2 weeks under 12 hours light-dark condition. From each rat, right uterine horn was excised under general anesthesia with sevoflurane and ketamine hydrochloride, and a tissue piece sizing 5 mm×5 mm was prepared therefrom. The tissue piece was subjected to autotransplantation such that the endometrium surface is attached to peritoneum.

From 24 hours after the preparation of the endometriosis model rats, commercially available clarithromycin tablets (trademark "Clarith Tablet 50 for Children" prepared by Taisho Pharmaceutical Co., Ltd) were orally administered to the rats for 3 days. The dose of administration was 10 mg/kg per day in terms of clarithromycin. Clarithromycin was not administered to control animals. Seven days after the preparation of the model rats, at which the model lesion reached its peak, the peritoneum tissue including the graft up to the abdominal muscle was excised to obtain a lesion sample. From the thus obtained samples, light microscope specimens (hematoxylin-eosin staining, toluidine blue staining) and electron microscope specimens (uranium-lead double staining) were prepared, and the existence of invaded mast cells, which is a symptom of endometriosis, and the degree of interstitial proliferative lesion were observed.

As a result, in the control group, invasion of mast cells and interstitial proliferative lesion were observed. In contrast, in the clarithromycin-administered group, invasion of mast cells was not observed, and the degree of interstitial proliferative lesion was apparently reduced.

EXAMPLE 2

Therapeutic Effect for Endometriosis by Roxithromycin

The same procedures as in Example 1 were repeated except that roxithromycin (trademark "Rulid Tablet 150", commercially available from Eisai Co., Ltd.) was used in place of clarithromycin. The administration dose was 6 mg/kg per day in terms of roxithromycin. As a result, in the control group, invasion of mast cells and interstitial proliferative lesion were observed. In contrast, in the roxithromycin-administered group, invasion of mast cells was not observed, and the degree of interstitial proliferative lesion was apparently reduced.

EXAMPLE 3

Therapeutic Effect for Endometriosis by Azithromycin

The same procedures as in Example 1 were repeated except that azithromycin (trademark "Zithromax Tablet 250 mg", commercially available from Pfizer Pharmaceuticals Inc.) was used in place of clarithromycin. The administration dose was 10 mg/kg per day in terms of roxithromycin. As a result, in the control group, invasion of mast cells and interstitial proliferative lesion were observed. In contrast, in the azithromycin-administered group, invasion of mast cells was not observed, and the degree of interstitial proliferative lesion was apparently reduced.

The invention claimed is:

1. A method for therapy of endometriosis and/or hysteromyoma, comprising administering a macrolide antibiotic to a patient suffering from endometriosis and/or hysteromyoma, in an amount effective for the therapy of endometriosis and/or hysteromyoma.

2. The method according to claim 1, wherein said macrolide antibiotic is clarithromycin, roxithromycin or azithromycin.

3. The method according to claim 1 or 2, wherein said macrolide antibiotic in an amount effective for the therapy of endometriosis is administered to a patient suffering from endometriosis.

* * * * *